(12) United States Patent
Martin et al.

(10) Patent No.: US 7,674,275 B2
(45) Date of Patent: Mar. 9, 2010

(54) SUTURE ANCHOR

(75) Inventors: David T. Martin, Milford, OH (US); Michael S. Cropper, Edgewood, KY (US); John J. Price, Seneca, SC (US); Richard F. Schwemberger, Cincinnati, OH (US); John L. Stammen, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 499 days.

(21) Appl. No.: 11/538,975

(22) Filed: Oct. 5, 2006

(65) Prior Publication Data
US 2008/0086172 A1  Apr. 10, 2008

(51) Int. Cl.
*A61B 17/04* (2006.01)
(52) U.S. Cl. .............. 606/232; 606/148; 24/115 R; 24/128; 24/129 R; 24/130
(58) Field of Classification Search ............. 606/232, 606/148; 24/115 R, 128, 129 R, 130
See application file for complete search history.

(56) References Cited

U.S. PATENT DOCUMENTS

| | | | |
|---|---|---|---|
| 2,443,335 A | 6/1948 | Vogel | |
| 2,854,648 A * | 9/1958 | Berg | 439/867 |
| 3,053,930 A * | 9/1962 | Mallanik et al. | 174/94 R |
| 3,337,682 A * | 8/1967 | Swett | 174/135 |
| 3,404,368 A * | 10/1968 | Roberts et al. | 439/866 |
| 3,952,377 A * | 4/1976 | Morell | 24/136 R |
| 4,235,238 A | 11/1980 | Ogiu et al. | |
| 4,455,717 A * | 6/1984 | Gray | 24/115 R |
| 4,669,473 A | 6/1987 | Richards et al. | |
| 4,741,330 A | 5/1988 | Hayhurst | |
| 4,790,812 A | 12/1988 | Hawkins, Jr. et al. | |
| 4,808,164 A | 2/1989 | Hess | |
| 4,998,495 A * | 3/1991 | Bos et al. | 114/218 |
| 5,037,422 A | 8/1991 | Hayhurst et al. | |
| 5,041,129 A * | 8/1991 | Hayhurst et al. | 606/232 |
| 5,046,513 A * | 9/1991 | Gatturna et al. | 128/898 |
| 5,119,607 A * | 6/1992 | Horning et al. | 52/147 |
| 5,217,458 A | 6/1993 | Parins | |
| 5,269,809 A * | 12/1993 | Hayhurst et al. | 606/232 |
| 5,341,823 A | 8/1994 | Manosalva et al. | |

(Continued)

FOREIGN PATENT DOCUMENTS

EP  823240  2/1998

(Continued)

OTHER PUBLICATIONS

PCT Search Report dated Jun. 25, 2008 for corresponding patent application, International Patent Application No. PCT/US2007/080388.

*Primary Examiner*—(Jackie) Tan-Uyen T. Ho
*Assistant Examiner*—Son Dang

(57) ABSTRACT

A suture anchor comprises an elongate body having a first end, a second end, and a longitudinal axis extending between the first and second ends. The first end may have a flared geometry. A lateral suture relief is in the elongate body extending from the first end to an longitudinal position intermediate the first and second ends. A hollow tubular portion in the elongate body is longitudinally spaced from the lateral suture relief. A suture is positioned in the hollow tubular portion. The suture has a delivery position parallel the longitudinal axis and a deployed position transverse to the longitudinal axis.

19 Claims, 6 Drawing Sheets

U.S. PATENT DOCUMENTS

| | | | |
|---|---|---|---|
| 5,383,905 A * | 1/1995 | Golds et al. ............... 606/232 |
| 5,403,348 A * | 4/1995 | Bonutti ..................... 606/232 |
| 5,464,425 A * | 11/1995 | Skiba ........................ 606/232 |
| 5,470,337 A | 11/1995 | Moss |
| 5,542,462 A * | 8/1996 | Elsenheimer et al. .. 160/178.1 R |
| 5,591,202 A | 1/1997 | Slater et al. |
| 5,626,614 A * | 5/1997 | Hart ........................ 606/232 |
| 5,755,730 A | 5/1998 | Swain et al. |
| 5,791,022 A * | 8/1998 | Bohman ........................ 24/130 |
| 5,800,445 A * | 9/1998 | Ratcliff et al. ............. 606/116 |
| 5,899,921 A | 5/1999 | Caspari et al. |
| 5,902,321 A | 5/1999 | Caspari et al. |
| 5,948,002 A * | 9/1999 | Bonutti ..................... 606/232 |
| 5,954,747 A | 9/1999 | Clark |
| 6,068,648 A | 5/2000 | Cole et al. |
| 6,086,608 A * | 7/2000 | Ek et al. .................... 606/232 |
| 6,200,329 B1 | 3/2001 | Fung et al. |
| 6,231,592 B1 | 5/2001 | Bonutti et al. |
| 6,306,159 B1 * | 10/2001 | Schwartz et al. ........... 606/232 |
| 6,500,184 B1 | 12/2002 | Chan et al. |
| 6,524,317 B1 * | 2/2003 | Ritchart et al. ............. 606/232 |
| 6,524,328 B2 | 2/2003 | Levinson |
| 6,566,484 B2 | 5/2003 | Gharda et al. |
| 6,645,227 B2 * | 11/2003 | Fallin et al. ................ 606/232 |
| 6,663,639 B1 | 12/2003 | Laufer et al. |
| 6,699,263 B2 | 3/2004 | Cope |
| 6,770,076 B2 * | 8/2004 | Foerster ..................... 606/326 |
| 6,881,816 B2 | 4/2005 | Gharda et al. |
| 6,909,015 B2 | 6/2005 | Kemmish et al. |
| 7,112,207 B2 | 9/2006 | Allen et al. |
| 7,556,640 B2 * | 7/2009 | Foerster ..................... 606/326 |
| 2001/0044639 A1 * | 11/2001 | Levinson ................... 606/228 |
| 2003/0158581 A1 | 8/2003 | Levinson |
| 2003/0163160 A1 | 8/2003 | O'Malley et al. |
| 2003/0171760 A1 | 9/2003 | Gambale |
| 2003/0191497 A1 | 10/2003 | Cope |
| 2004/0093023 A1 | 5/2004 | Allen et al. |
| 2004/0122473 A1 | 6/2004 | Ewers et al. |
| 2004/0133238 A1 | 7/2004 | Cerier |
| 2004/0153103 A1 * | 8/2004 | Schwartz et al. ............ 606/148 |
| 2004/0186514 A1 * | 9/2004 | Swain et al. ................. 606/224 |
| 2004/0260344 A1 | 12/2004 | Lyons et al. |
| 2005/0033366 A1 | 2/2005 | Cole et al. |
| 2005/0234512 A1 | 10/2005 | Nakao |
| 2005/0251157 A1 | 11/2005 | Saadat et al. |
| 2005/0251202 A1 | 11/2005 | Ewers et al. |
| 2006/0009789 A1 | 1/2006 | Gambale et al. |
| 2006/0015125 A1 | 1/2006 | Swain |
| 2006/0025819 A1 * | 2/2006 | Nobis et al. ................ 606/232 |
| 2006/0079914 A1 | 4/2006 | Modesitt et al. |
| 2006/0106405 A1 | 5/2006 | Fann et al. |

FOREIGN PATENT DOCUMENTS

| | | |
|---|---|---|
| EP | 746239 | 9/2002 |
| EP | 1447052 | 8/2004 |
| EP | 1632186 | 6/2008 |
| JP | 2004358045 | 12/2004 |
| WO | 9422381 | 10/1994 |
| WO | 01/89393 | 11/2001 |
| WO | WO 02094108 | 11/2002 |
| WO | WO 2005/065412 A2 | 7/2005 |
| WO | WO 2007/059068 A1 | 5/2007 |

* cited by examiner

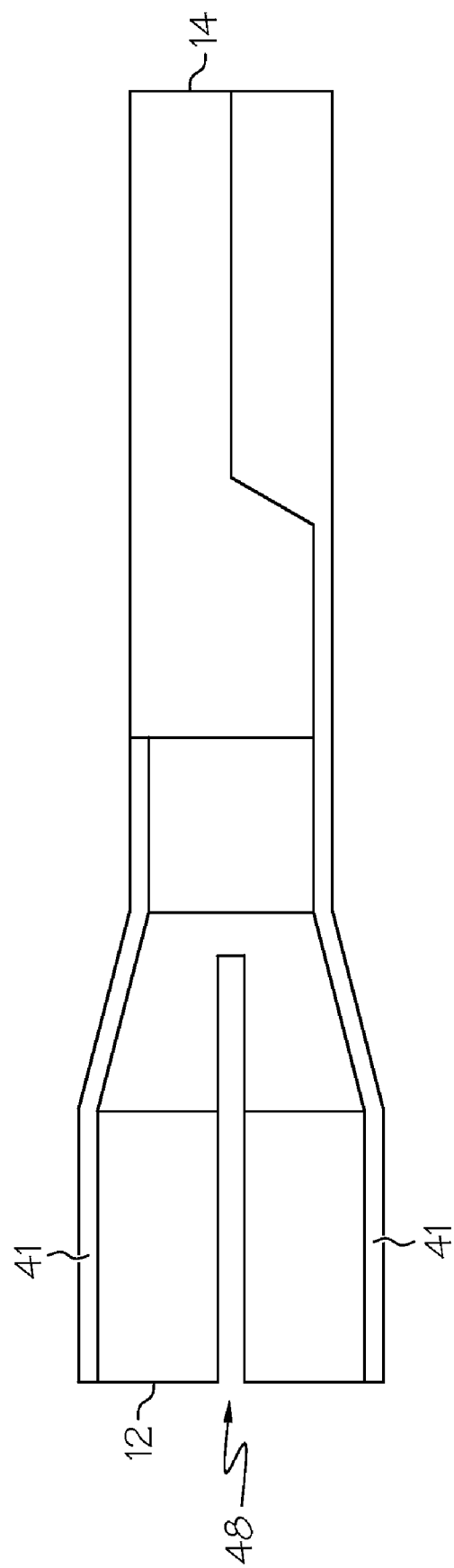

SUTURE ANCHOR

BACKGROUND

The following disclosure relates to surgery, and more particularly to suture anchors used during surgery. Surgery generally refers to the diagnosis or treatment of injury, deformity, or disease. A wide variety of surgical techniques have been developed. One type of surgery is called minimally invasive surgery, which typically involves entering the body through the skin or through a body cavity or anatomical opening while minimizing damage to these structures. Minimally invasive medical procedure usually involve less operative trauma for the patient compared to open surgical procedures. Minimally invasive surgical procedures are also generally less expensive, reduces hospitalization time, causes less pain and scarring, and reduces the incidence of complications related to the surgical trauma, thus speeding the recovery.

Endoscopes are often used during minimally invasive surgical procedure to visualize the organs and structures inside the body. Endoscopes generally use a light delivery system to illuminate the tissue under inspection. Typically the light source is outside the body and the light is typically directed via an optical fiber system. Images are captured, usually through a lens system, and transmitting to a monitor. Some endoscopes include working channels through which medical instruments may be introduced into the body to biopsy or operate. Working channels can also be independent of the endoscope. Endoscopes may be rigid or flexible. Some flexible endoscopes are steerable to facilitate positioning the endoscope in the body.

Sutures are often used during surgical procedures to hold skin, internal organs, blood vessels, and other tissues in the body. A suture is typically an elongate flexible filament, but may take a variety as different thread or thread-like structures, including without limitation fibers, lines, wires, and the like. A suture may be a homogeneous or heterogeneous, and may also comprise a single filament or a composite suture, such as a two or more twisted or woven filaments. In addition, a suture may be made from a wide array of absorbable (i.e., metabolized by the body) or non-absorbable materials known in the art.

A variety of different techniques and devices have been developed to deliver and attached sutures to tissue. Some techniques involve piercing tissue with needles, tying or forming knots or loops, delivering anchors such as t-tags, x-tags and other flexible or rigid anchors, and the like. Disclosed and claimed herein are novel delivery and attachment techniques and devices for anchoring sutures.

BRIEF DESCRIPTION OF DRAWINGS

While the specification concludes with claims that particularly point out and distinctly claim the invention, it is believed the invention will be better understood from the following description taken in conjunction with the accompanying drawings illustrating some non-limiting examples of the invention. Unless otherwise indicated, like reference numerals identify the same elements.

FIG. 6 depicts side view of an anchor.

DETAILED DESCRIPTION

Figure 1:
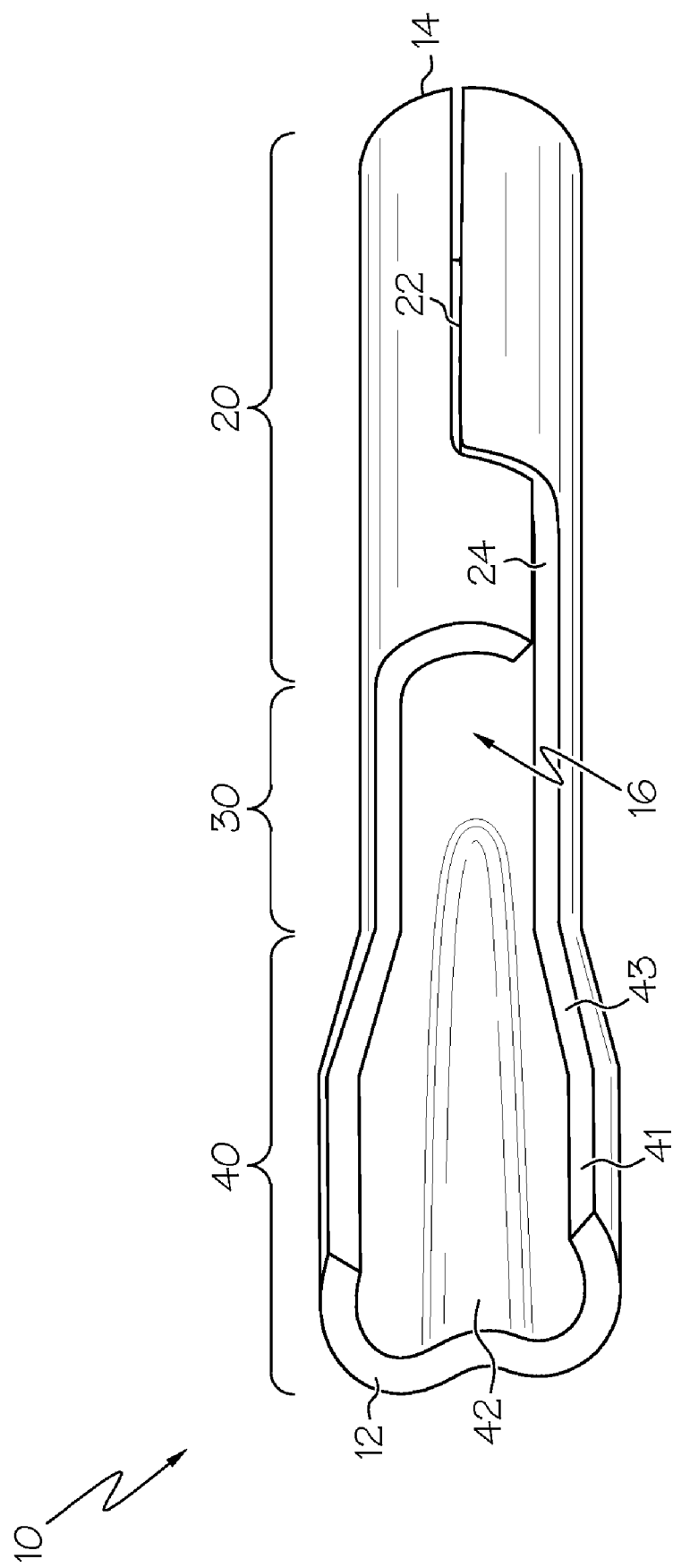
FIG. 1 depicts a perspective view of an anchor.
Figure 2:
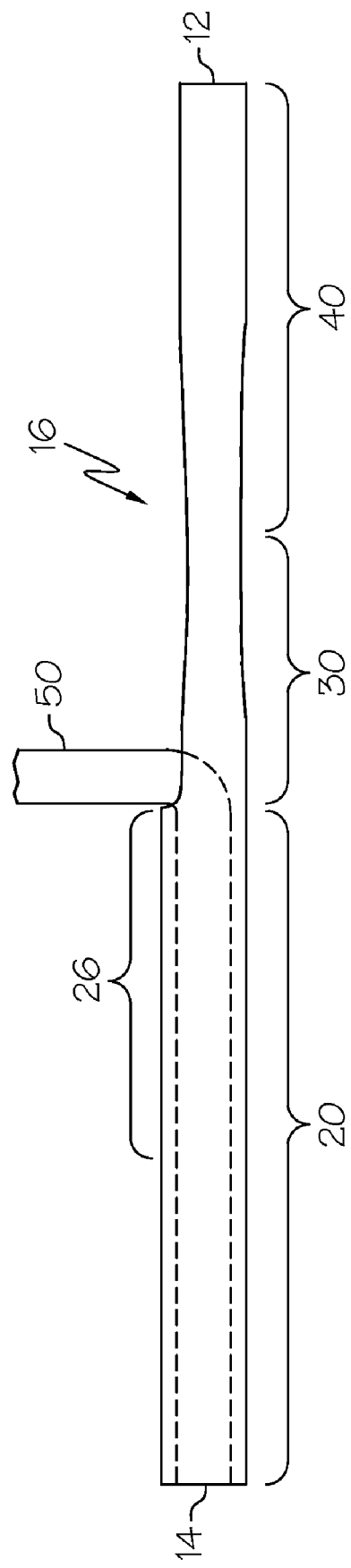
FIG. 2 depicts side view of an anchor with a suture shown partially in phantom.

FIGS. 1-2 illustrate an example of an suture anchor. The anchor has an elongate body (10) comprising a first end (12), a second end (14), and a longitudinal axis extending between the first and second ends. In this example the longitudinal axis is straight, but bowed or curved axes are also contemplated. The length of the body (10) may vary widely, but in this example the body length is about 0.4 inches. The body (10) in this embodiment comprises a first portion (20), a second portion (30) connected to the first portion (20), and a third portion (40) connected to the second portion (30).

The first portion (20) comprises a hollow tubular section with an outside diameter. While the outside diameter can vary widely, in this example the diameter is about 0.025 inches. In this example the tubular section is substantially circular and has a substantially constant outside diameter; however, other geometries may also be used. In this example the length of the first portion (20) is less than the half the length of the body (10). Also in this example the hollow tubular section comprises a longitudinal seam (22) and an offset stepped portion (24).

The second portion (30) is intermediate the first and third portions (20, 40). In this example the second portion (30) comprises a section with an outside diameter substantially the same as the first portion (20). The second portion (30) also includes a lateral relief (16).

The third portion (40) comprises a flared geometry (41) and a transitional geometry (43). The flared geometry (41) is spaced laterally outward relative the first and second portions (20, 30). The flared geometry (41) provides an interference fit within a needle thus providing a fictional resistance to prevent the body (10) from unintentionally ejecting from the needle. While the number and shape of a flared geometry (41) may vary widely, the flared geometry (41) in the present example has two symmetrical wings space from one another such that the outside diameter is greater than the first and second portions (20, 30). A longitudinal rib (42) extends from the first end (12), resulting the third portion (40) having a generally W-shaped cross-section. The transitional geometry (43) tapers medially to the diameter of the second portion (30).

The anchor body (10) comprises a lateral relief (16) extending from the first end (12) to a longitudinal position intermediate the first and second ends (12, 14). In this example, the lateral relief (16) is on the second and third portions (30, 40), and terminates at the first portion (20). Thus, the first portion (20) is longitudinally spaced from the lateral relief (16). The relief (16) is dimensioned to allow the suture (50) to pass laterally through the relief (16). In this example the relief (16) has about a 110 degree opening in the second portion (30), and about a 0.022 inch opening at the flared geometry (41). The suture (50) has a delivery position where the suture (50) is coextensive with longitudinal axis of the body (10) and positioned at least partially within the second and third portions (30, 40). The suture (50) also has a deployed position, as depicted in FIG. 2, where the suture extends transverse from the body (10). As shown in this example, the suture (50) extends transverse to the longitudinal axis of the body (10) and at the center point of the body (10).

A suture (50) is threaded into the first portion (20) and attached to the hollow tubular section. In one embodiment the suture (50) may be fixedly attached by crimping the tubular section about the suture (50). While the crimp can be positioned in a number of different locations, preferably the crimp is positioned away from the second end (14) at some point in the area (26). Naturally, alternative attaching mechanisms may also be employed, such as using adhesives, thermal interferences, welding, and the like. Any excess suture (50) extending beyond the second end (14) may be severed even with second end (14). In an alternative embodiment the suture (50) may be attached to the second end (14) by passing the suture (50) through the hollow tubular section and tying a knot. In yet another embodiment the suture (50) may be slideably attached in the hollow tubular section.

Figure 3:
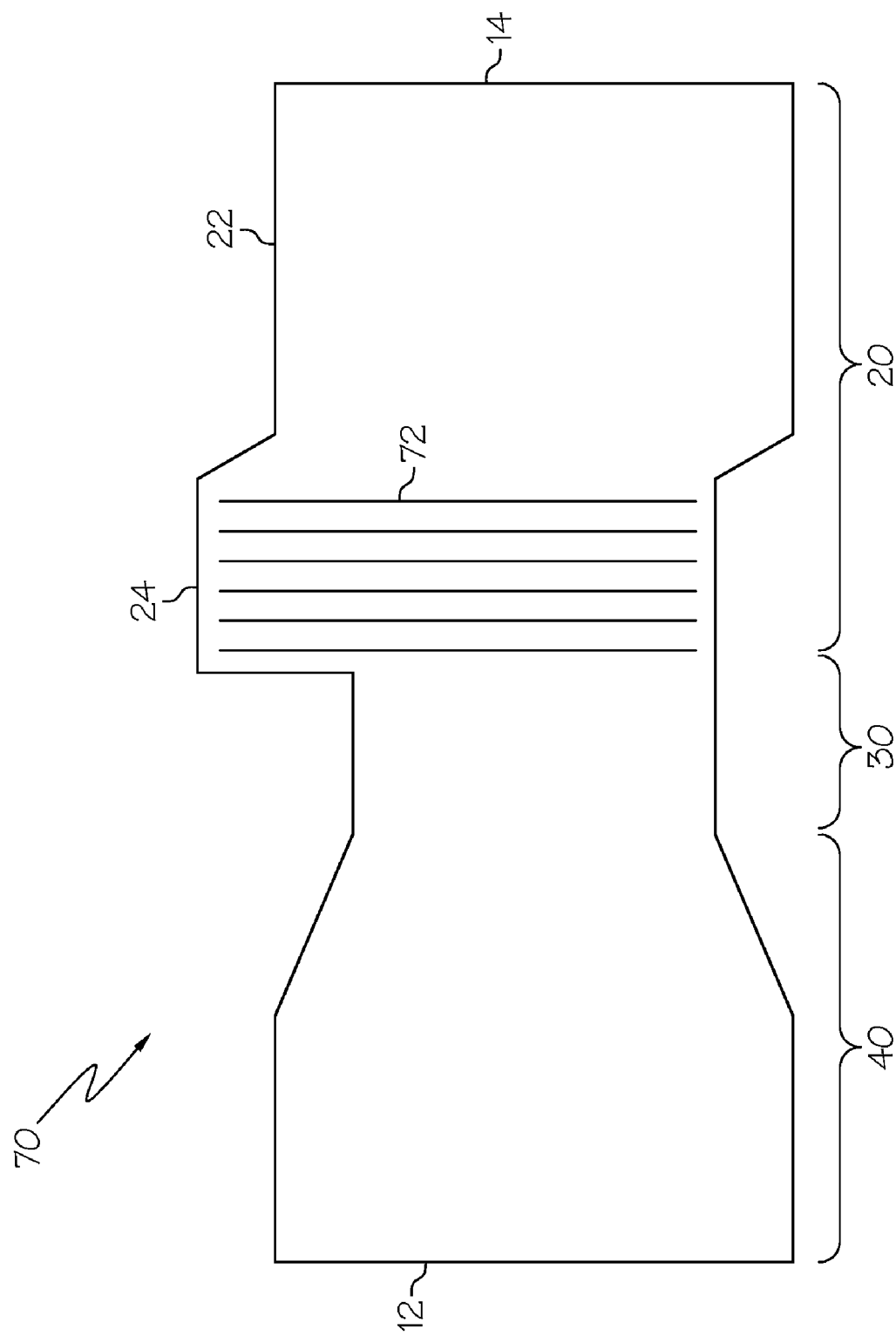
FIG. 3 depicts a sheet from which an anchor may be formed.

The anchor body (10) can be made from a wide range of materials, including metals, plastics, ceramics, composites, and the like. In this example the body (10) is formed by stamping a sheet of 316 stainless steel. As shown in FIG. 3, a sheet (70) of about 0.005 inches in thickness is cut to the appropriate profile to form the various features of the body (10). Optionally, teeth (72) may be added, such as in a stamping operation, to facilitate good mechanical grasping of the suture (50). Preferably the teeth (72) are positioned adjacent the location of the crimp. The sheet is then introduced to a stamp and die operation to form the body (10). Alternatively, the teeth (72) are formed at the same time as the stamp and die operation.

Figure 4:
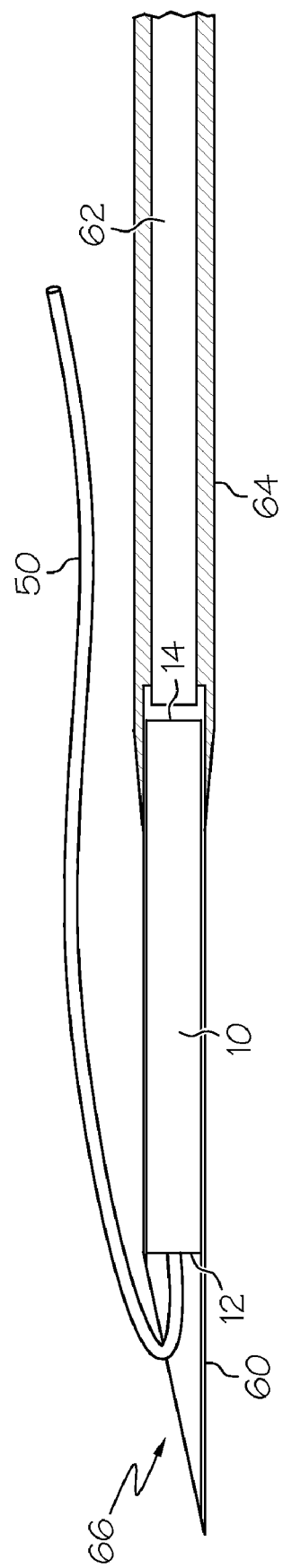
FIG. 4 depicts a cross-sectional side view an anchor delivery needle, with the anchor depicted schematically.

FIG. 4 illustrates one of many potential configurations and techniques to deliver a suture anchor. A hollow needle (60) is attached to a flexible shaft (64). The needle (60) and shaft (64) are sized to fit in an working channel on a steerable flexible endoscope. An anchor body (10) and suture (50) are positioned in the needle (60). The body (10) is illustrated schematically, and in this example the first end (12) is positioned as the leading end and the second end (14) is positioned as the trailing end. As shown in this example, the suture (50) is in its delivery position and extends out of the distal end (66). After positioning the endoscope to a desired position in a patient, the needle (60) and suture (50) may be threaded into proximal end of the working channel. A handle (not shown) is operatively connected to the flexible shaft (64). Optionally, a retractable sheath (not shown) may be positioned over the distal end (66) to prevent snagging within the working channel. After pushing the flexible shaft (64) the length of the working channel, the needle (60) may be extended distally from the working channel and penetrated into a target tissue. By continuing the advance the flexible shaft (64), the needle (60) depth may be controlled for transmural penetration or intramural penetration. A flexible push rod (62), such a nitinol wire, is positioned in the flexible shaft (64) and is operably connected to the handle. Once the distal end (66) is positioned in its desired depth, the push rod (62) may be actuated to slide axially relative the shaft (64) to engage and push the body (10) out from the distal end (66). Like a traditional t-tag, once ejected the anchor body (10) will tend to rotate to transverse angle relative the needle (60) puncture and the suture (50) will shift to its deployed position. As such, the suture (50) will be anchored to the tissue. The needle (60) and shaft (64) may then be withdrawn from the working channel leaving the suture (50) anchored in the tissue with the suture (50) in the working channel for subsequent manipulation as the surgeon may desire.

While the suture anchor was illustrated in a minimally invasive procedure with a flexible endoscope, rigid scopes could also utilize the suture anchor. Further the suture anchor could be used in non-minimally invasive procedures.

Figure 5:
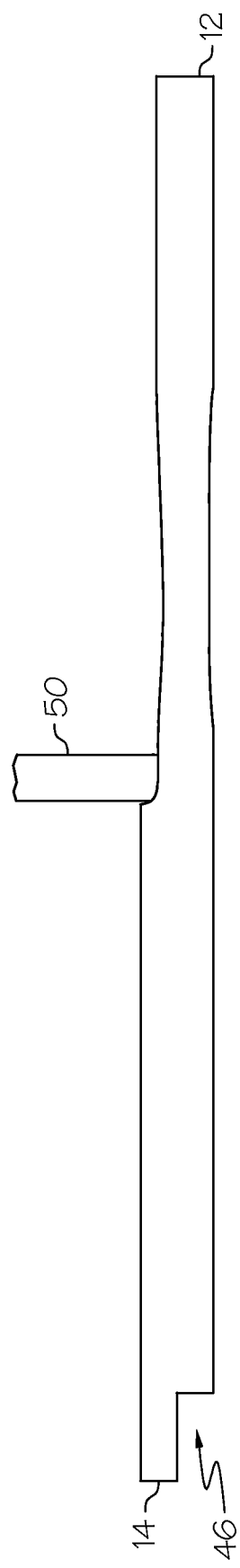
FIG. 5 depicts side view of an anchor.

FIG. 5 illustrates a variation where a notch (46) is added to the second end (14). In this embodiment the step or notch (46) is dimensioned to mate with the geometry of the first end (12). Thus, multiple anchors could be loaded in a needle in tandem. The mating preferably facilitates axial transmission of a load introduced by a push rod in the needle. By incrementally advancing a push rod, the surgeon may selectively deploy anchors one at a time during a procedure.

FIG. 6 illustrates a variation where the longitudinal rib is removed and replaced with a longitudinal slot (48). The slot (48) provides a relief thus allowing the flared geometry (41) to deflect medially. Preferably the body (10) will be made from a resilient material, such as stainless steel, so that after the deflection the flared geometry (41) will be biased laterally.

Preferably, the foregoing devices will be processed before surgery. First, a new or used device is obtained and if necessary cleaned. The device can then be sterilized. In one sterilization technique, the device is placed in a closed and sealed container, such as a plastic or TYVEK bag. The container and device are then placed in a field of radiation that can penetrate the container, such as gamma radiation, x-rays, or high-energy electrons. The radiation kills bacteria on the device and in the container. The sterilized device can then be stored in the sterile container. The sealed container keeps the device sterile until it is opened in the medical facility.

Having shown and described various embodiments and examples, further adaptations of the methods and apparatuses described herein can be accomplished by appropriate modifications by one of ordinary skill in the art without departing from the scope of the present invention. Several of such potential modifications have been mentioned, and others will be apparent to those skilled in the art. For instance, the specific dimensions described above and scales depicted in the figures will be understood to be non-limiting examples. Accordingly, the scope of the present invention should be considered in terms of the following claims and is understood not to be limited to the details of structure, materials, or acts shown and described in the specification and figures.

The invention claimed is:

1. A suture anchor, comprising:
   a) an elongate body comprising a first end, a second end, and a longitudinal axis extending between the first and second ends, the first end comprising a flared geometry;
   b) a lateral suture relief in the elongate body, the relief extending from the first end to a longitudinal position intermediate the first and second ends;
   c) a hollow tubular portion in the elongate body, the hollow tubular portion being longitudinally spaced from the lateral suture relief, and
   d) a suture positioned in the hollow tubular portion, the suture having a delivery position parallel the longitudinal axis and a deployed position transverse to the longitudinal axis.

2. The suture anchor of claim 1, wherein the flared geometry comprises symmetrical wings.

3. The suture anchor of claim 1, wherein the suture is attached with a crimp.

4. The suture anchor of claim 3, further comprising teeth in the hollow tubular portion adjacent the location of the crimp.

5. The suture anchor of claim 1, wherein the first end further comprises a longitudinal rib.

6. The suture anchor of claim 5, wherein the first end has a generally W-shaped cross-section.

7. The suture anchor of claim 1, wherein the elongate body is formed by stamping a sheet of metal.

8. The suture anchor of claim 1, the second end comprises a geometry dimensioned to mate with the geometry of the first end.

9. The suture anchor of claim 1, wherein the suture is fixedly attached to the elongate body.

10. The suture anchor of claim 1, wherein the tubular portion has a substantially constant outside diameter.

11. The suture anchor of claim 10, wherein elongate body further comprises an intermediate portion between the tubular portion and the flared geometry, the intermediate portion having substantially the same outside diameter as the tubular portion and the suture relief extending onto the intermediate portion.

12. A anchor delivery device, comprising a flexible shaft having a distal end with a hollow needle for receiving the anchor of claim 1; a push rod positioned in the flexible shaft adapted to deploy the anchor from the needle; and a handle operatively connected to the flexible shaft and the push rod.

13. A suture anchor, comprising:
   a) an anchor body stamped from a sheet of metal, the anchor body comprising a first end and a second end;
   b) a lateral suture relief in the anchor body, the lateral suture relief extending from the first end to an longitudinal position intermediate the first and second ends;
   c) a hollow portion in the anchor body, the hollow portion being longitudinally spaced from the lateral suture relief, and
   d) a suture positioned in the hollow portion and fixedly attached to the anchor body.

14. The suture anchor of claim 13, wherein the hollow portion comprises a longitudinal seam.

15. The suture anchor of claim 14, wherein the seam comprises an offset stepped portion.

16. The suture anchor of claim 13, wherein the suture is fixedly attached with a crimp.

17. The suture anchor of claim 13, wherein anchor body comprises a flared geometry.

18. A suture anchor, comprising:
   a) a first portion comprising a hollow tubular section with an outside diameter, a suture being positioned in the tubular section;
   b) a second portion connected to the first portion, the second portion comprising a section with an outside diameter substantially the same as the first portion;
   c) a third portion connected to the second portion, the third portion comprising a flared geometry spaced laterally outward relative the first portion; and
   d) a lateral suture relief on the second and third portions.

19. The suture anchor of claim 18, wherein the tubular section is circular.

* * * * *